(12) United States Patent
Hecker et al.

(10) Patent No.: US 7,347,888 B2
(45) Date of Patent: Mar. 25, 2008

(54) AIR PURIFIER

(75) Inventors: Steve Hecker, Santa Monica, CA (US); Dale Honda, Torrance, CA (US)

(73) Assignee: Sylmark Holdings Limited (IE)

( * ) Notice: Subject to any disclaimer, the term of this patent is extended or adjusted under 35 U.S.C. 154(b) by 0 days.

(21) Appl. No.: 11/380,872

(22) Filed: Apr. 28, 2006

(65) Prior Publication Data

US 2006/0196360 A1  Sep. 7, 2006

Related U.S. Application Data

(60) Provisional application No. 60/676,492, filed on Apr. 29, 2005.

(51) Int. Cl.
*B03C 3/016* (2006.01)

(52) U.S. Cl. .................. 96/16; 96/224; 422/186.04; 422/186.3

(58) Field of Classification Search .............. 96/16, 96/224, FOR. 175; 95/57; 422/186.04, 422/186.3
See application file for complete search history.

(56) References Cited

U.S. PATENT DOCUMENTS

| | | | | |
|---|---|---|---|---|
| 3,217,470 A | * | 11/1965 | Omohundro | 96/224 |
| 3,804,942 A | * | 4/1974 | Kato et al. | 423/239.1 |
| 5,632,806 A | * | 5/1997 | Galassi | 96/16 |
| 6,048,499 A | * | 4/2000 | Hirayama | 422/121 |
| 6,149,717 A | * | 11/2000 | Satyapal et al. | 96/16 |
| 6,673,137 B1 | * | 1/2004 | Wen | 96/224 |
| 6,752,970 B2 | * | 6/2004 | Schwartz et al. | 422/186.3 |
| 6,911,177 B2 | * | 6/2005 | Deal | 422/24 |
| 6,955,708 B1 | * | 10/2005 | Julos et al. | 95/59 |
| 7,156,897 B2 | * | 1/2007 | Wen | 95/28 |
| 2002/0020297 A1 | * | 2/2002 | Harris et al. | 95/273 |
| 2003/0165410 A1 | * | 9/2003 | Taylor | 422/186.04 |
| 2003/0183503 A1 | * | 10/2003 | Fujii | 204/157.3 |
| 2003/0206840 A1 | * | 11/2003 | Taylor et al. | 422/186.04 |
| 2004/0007134 A1 | * | 1/2004 | Parsa | 96/16 |
| 2004/0047776 A1 | * | 3/2004 | Thomsen | 422/186.07 |
| 2004/0226447 A1 | * | 11/2004 | Lau et al. | 96/16 |
| 2005/0194246 A1 | * | 9/2005 | Botvinnik et al. | 204/164 |
| 2005/0269199 A1 | * | 12/2005 | Pollak et al. | 204/164 |
| 2006/0005707 A1 | * | 1/2006 | Yuen | 96/16 |

FOREIGN PATENT DOCUMENTS

WO    WO 03/078571 A2 *  9/2003

* cited by examiner

*Primary Examiner*—Richard L. Chiesa
(74) *Attorney, Agent, or Firm*—Kathy Mojibi Kavcioglu

(57) ABSTRACT

An air purifier is disclosed having an electrostatic chamber and a germicidal chamber, wherein the two chambers are distinct and there is no air flow communication between the electrostatic and germicidal chambers.

15 Claims, 3 Drawing Sheets

AIR PURIFIER

RELATED APPLICATION

This application is related to provisional application No. 60/676,492 filed on Apr. 29, 2005.

FIELD OF INVENTION

The present invention relates generally to air purifiers and more particularly to an air purifier that conditions the air utilizing electrostatic and germicidal mechanisms.

BACKGROUND OF THE INVENTION

Various devices are available for purifying the air in a room. One type of room air purifier that is widely known and used is an electrostatic air cleaner. Electrostatic air cleaners use electric energy to generate electrostatic forces which create air flow without the use of a fan or other moving parts. Electrostatic forces also enable the air cleaner to collect airborne contaminants such as dust, smoke, oil mist, pollen, pet dander and other small debris particles from the air circulated in dwellings, workplaces, and other structures.

Generally, known electrostatic air cleaners utilize two arrays of electrodes excited by high-voltage. In a known design, the first electrode array comprises wire or rod-shaped electrodes (hereinafter "wire electrodes"), while the second electrode array comprises plate electrodes. A high-voltage generator creates an electrical charge between the first and second electrode arrays.

The particulate matter enters the region of the first electrode array and is charged before entering the region of the second electrode array, where it is removed from the air stream. Specifically, due to the high-voltage charge at the wire electrodes, free electrons are stripped off of atoms and molecules in the surrounding air. These electrons migrate to the positively charged wire electrodes, where they are collected. The removal of free electrons leaves the stripped atoms and molecules positively charged, which are repelled from the positively charged wire electrodes and attracted to the negatively charged plate electrodes. The addition of the electrons from the negatively charged plate electrodes also produces negative air ions that are propelled from the trailing edge of the plate electrodes. Thus, the ionic forces exerted on atoms and molecules create a silent movement of air through the air cleaner.

It is also known to incorporate an ultraviolet lamp in the airflow of an electrostatic air cleaner to create a germicidal air cleaner. However, there are several deficiencies in the known designs of germicidal air cleaners. For example, the placement of the ultraviolet lamp in the electrostatic air flow interferes with the substantially linear electrostatic air flow from the air inlet to the air outlet, thus lowering the effectiveness of the electrostatic function of the air purifier. Furthermore, the germicidal lamp is most effective if the air flows in a longitudinal direction to the lamp because of the increased dwell time near the lamp. However, in known designs, the germicidal lamp is positioned such that the air flows transversely with respect to the lamp, thus lowering the germicidal effectiveness of the air purifier.

Accordingly, it is desirable to provide an air cleaner that has electrostatic and germicidal functions, wherein the air flows at a high rate with relatively low noise, and wherein the components are positioned such that the individual parts are easily accessible for cleaning and maintenance.

DETAILED DESCRIPTION OF THE PREFERRED EMBODIMENTS

Figure 1:
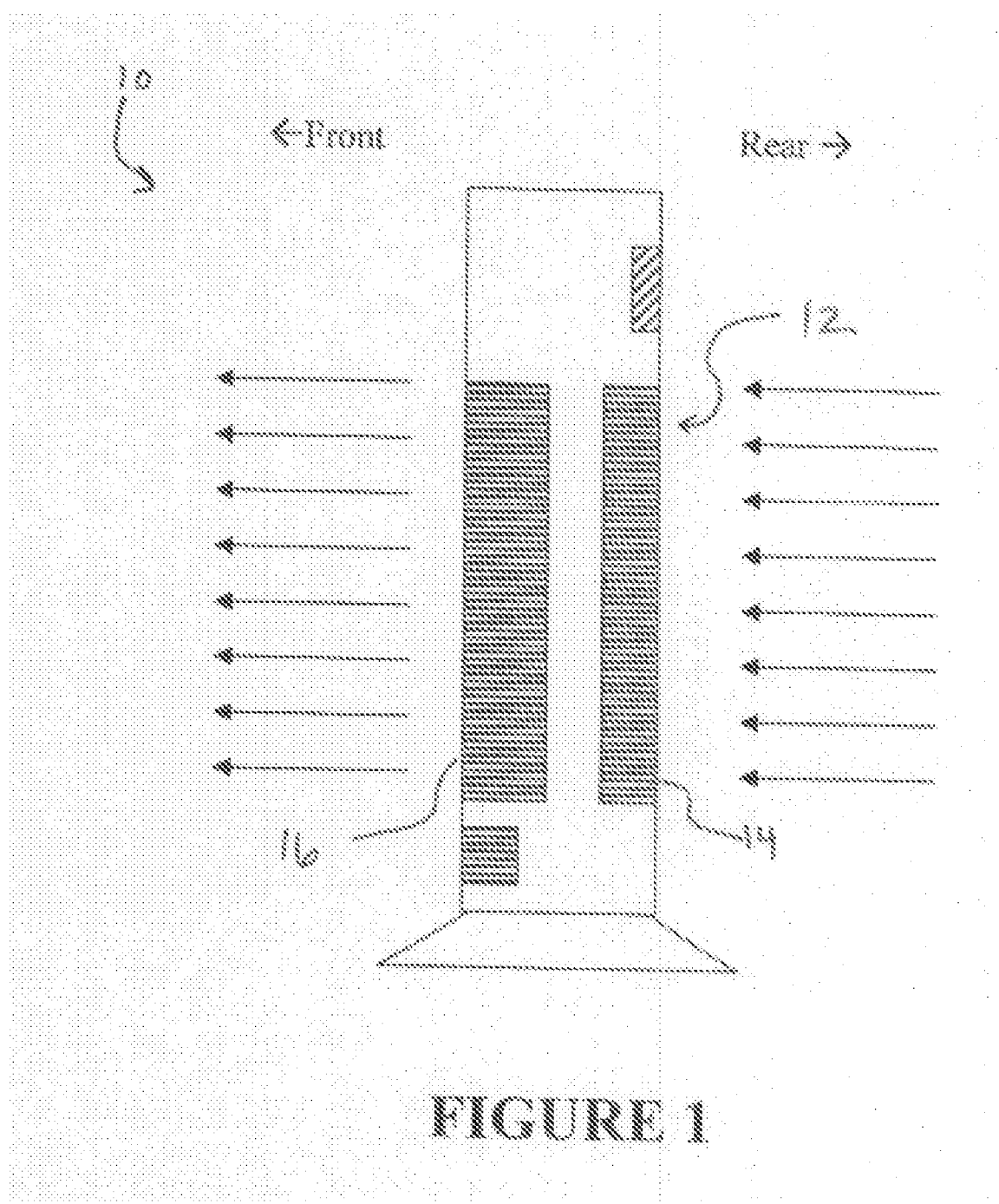
FIG. 1 is a schematic view of the airflow through the electrostatic chamber of a preferred embodiment of the air purifier of the present invention.

In the air purifier of the present invention, the electrostatic and germicidal UV air purification functions are conducted in separate, distinct chambers such that the air flow from the germicidal chamber will never mix with the air flow of the electrostatic chamber. FIG. 1 depicts a preferred embodiment of the airflow through the electrostatic chamber of the air purifier 10. As shown in FIG. 1, air enters the electrostatic chamber 12 of the air purifier 10 at the electrostatic chamber entrance 14. In a preferred embodiment of the invention, the electrostatic chamber entrance 14 is located at the back of the air purifier unit. Air exits the electrostatic chamber 12 at the electrostatic chamber exit 16, preferably located at the front of the air purifier unit 10. The air generally flows in a straight path.

Figure 2:
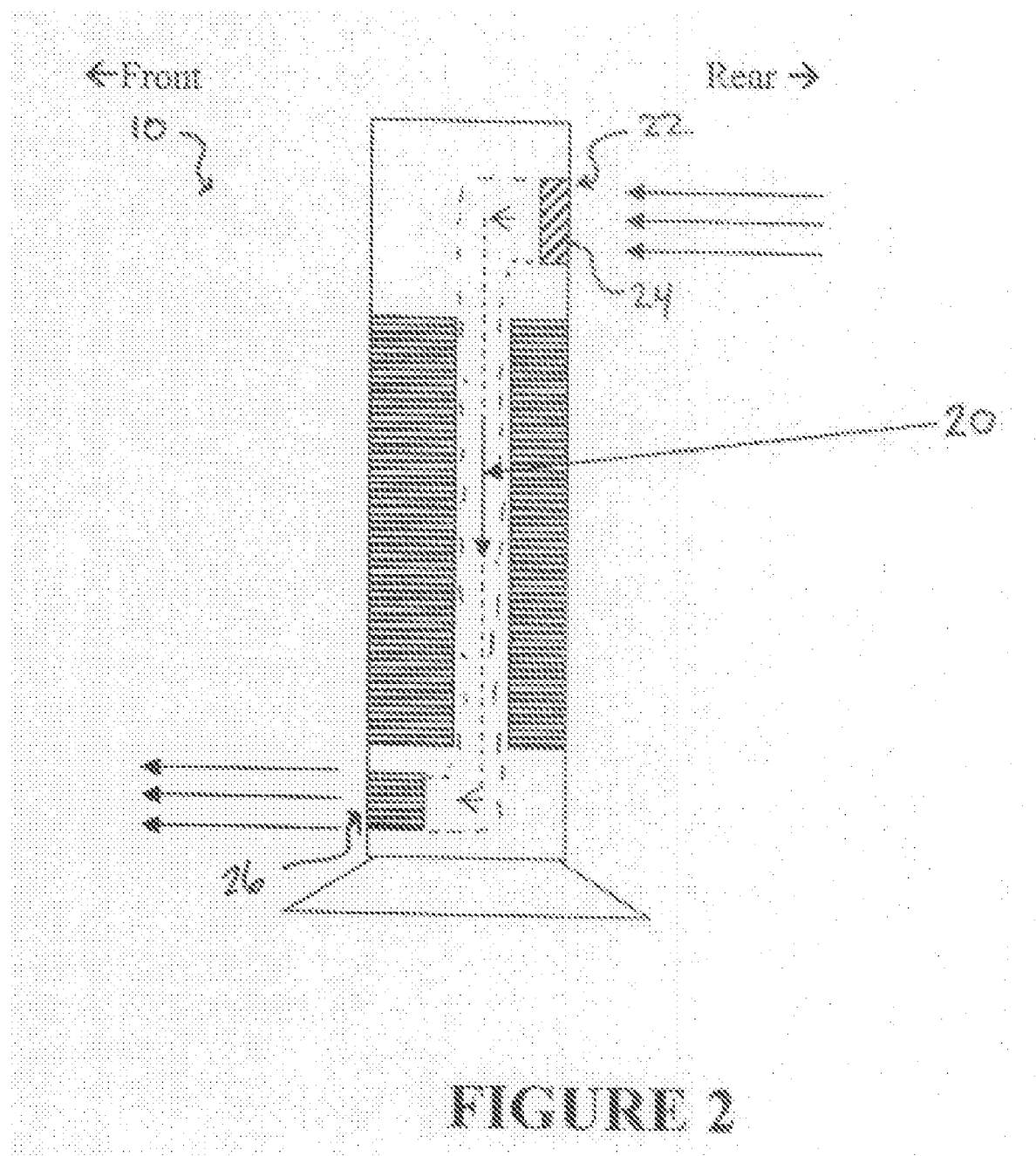
FIG. 2 is a schematic view of the airflow through the ultraviolet chamber of a preferred embodiment of the air purifier of the present invention.

The airflow through the UV chamber is shown in FIG. 2. Air enters the germicidal chamber 20 at the germicidal chamber entrance 22. In a preferred embodiment of the invention, the germicidal chamber entrance 22 is located at or near the top of the unit. A removable filter 24 can be provided at the germicidal chamber entrance 22 to capture larger particles. The air flows through the germicidal chamber 20 and exits at the germicidal chamber exit 26. In a preferred embodiment of the invention, the germicidal chamber exit 26 is located at or near the bottom of the air purifier unit 10. To assist with the flow of air through the germicidal chamber 20, a fan 30 is positioned near the bottom of the unit to pull the air in through the chamber. The positioning of the fan near the bottom of the unit offers several possible advantages, including, lowering the center of gravity for the unit, shorter wiring considerations, lower noise, and less dust load to fan blade, UV lamp and interior of unit. Furthermore, because the fan is downstream of the UV lamp (as will be discussed below), the UV lamp is cooled by the fan.

The electrostatic and germicidal chambers are distinct chambers such that the air flow from the germicidal chamber will never mix with the air flow of the electrostatic chamber. In the embodiment shown in FIGS. 1 and 2, the germicidal chamber 20 is positioned within the electrostatic chamber 12. However, the walls of the germicidal chamber prevent the air from the electrostatic chamber to enter the germicidal chamber. Similarly, the air in the germicidal chamber cannot escape to the electrostatic chamber.

Those skilled in the art will understand that the location of the chambers can vary. For example, the electrostatic 12 and germicidal 20 chambers can be positioned side by side. Accordingly, the present invention is not limited to the embodiment shown in the drawings. The invention encompasses any air purifier wherein the germicidal chamber and electrostatic chamber do not share air flow.

As the air travels from the germicidal chamber entrance 22 at the top of the unit to the germicidal chamber exit 26 at the bottom of the unit, it essentially travels through an air chamber 20 that is substantially vertical. The vertical germicidal air chamber 20 encloses a germicidal lamp (not shown), preferably an ultraviolet lamp. The vertical germicidal air chamber is more effective than a horizontal air chamber because it causes the air to dwell for a longer period of time at close range to the ultraviolet lamp. The increased dwell time for ultraviolet exposure increases the germicidal effect of the air purifier. Various types of germicidal lamps can be used with varying degrees of UV power output and rated life hours, as known by those skilled in the art. Germicidal effectiveness is a function of UV intensity, dwell time near UV radiation, targeted microbe, volume of air flow and other considerations. For maximum germicidal effectiveness, ultraviolet light is preferably provided at a wavelength of 254 nm.

The UV lamp should be positioned within the germicidal chamber 20 in a manner that protects the user from direct exposure to UV light while the lamp is in operation or while the lamp is in the process of being replaced or cleaned. To this effect, light baffling or shielding is provided. Furthermore, the housing 10 is equipped with interlocking devices that prevent the user from accessing the germicidal chamber 20, while the lamp is in operation.

Figure 3:
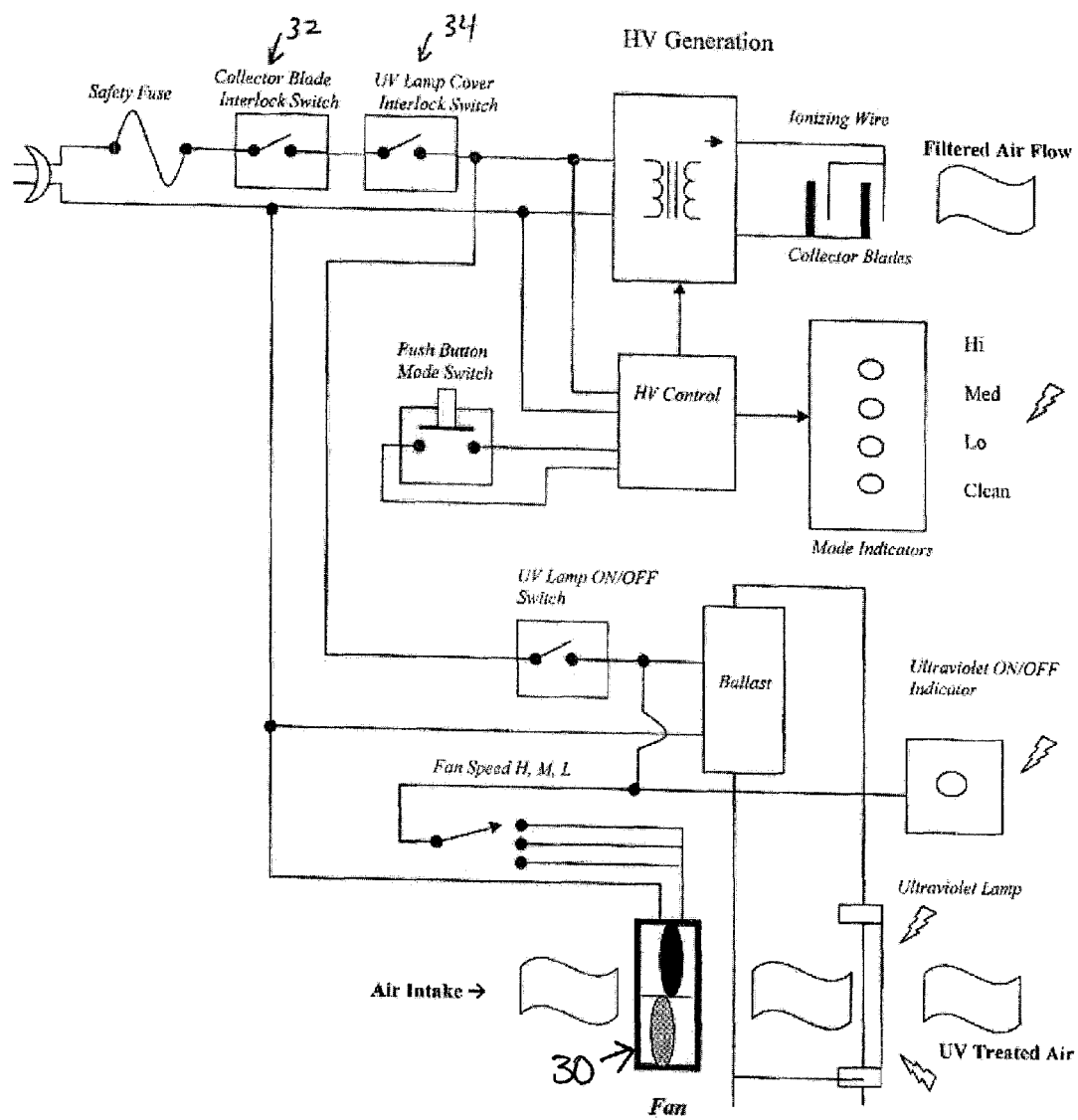
FIG. 3 is a schematic view of the components of a preferred embodiment of the air purifier of the present invention.

As shown in FIG. 3, the air purifier of the present invention is preferably equipped with safety interlock switches 32, 34. The collector blade interlock switch 32 prevents the unit from operating if the collector blades are not properly positioned in the unit. This feature protects the user from coming into contact with an open electric circuit. The UV lamp cover interlock switch 34 prevents the unit from operating if the UV lamp cover is not properly closed. This feature ensures that the cover is on when the UV lamp is operating, thus protecting the user from exposure to ultraviolet rays.

Many modifications and other embodiments of the invention set forth herein will come to mind to one skilled in the art to which the invention pertains having the benefit of the teachings presented in the foregoing descriptions and the associated drawings. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

The invention claimed is:

1. An air purifier, comprising:
   a housing, having a top, bottom, front and back; an electrostatic chamber wherein the electrostatic chamber has an electrostatic chamber entrance at the back of the housing and an electrostatic chamber exit at the front of the housing;
   a germicidal chamber wherein the germicidal chamber has a germicidal chamber entrance near the top of the housing and a germicidal chamber exit near the bottom of the housing; and
   wherein there is no air flow communication between the electrostatic and germicidal chambers.

2. The air purifier of claim 1, wherein:
   the electrostatic chamber comprises a first electrode array, a second electrode array and a first air stream moving in a direction from the first electrode array toward the second electrode array; and
   the germicidal chamber comprising a germicidal lamp and a second air stream.

3. The air purifier of claim 2 wherein the second air stream moves in a substantially vertical direction.

4. The air purifier of claim 2 wherein the first air stream moves in a substantially horizontal direction.

5. The air purifier of claim 1, further comprising a fan positioned in the germicidal chamber.

6. The air purifier of claim 5 wherein the fan is positioned near the bottom of the housing.

7. The air purifier of claim 1 wherein the germicidal chamber is positioned within the electrostatic chamber.

8. The air purifier of claim 1 wherein the germicidal chamber and the electrostatic chamber are positioned side-by-side.

9. An air purifier, comprising:
   a housing, having a top, bottom, front and back;
   an electrostatic chamber comprising a first electrode array, a second electrode array and a first air stream moving in a direction from the first electrode array toward the second electrode array, wherein the electrostatic chamber has an electrostatic chamber entrance at the back of the housing and an electrostatic chamber exit at the front of the housing;
   a germicidal chamber comprising a germicidal lamp and a second air stream, wherein the germicidal chamber has a germicidal chamber entrance near the top of the housing and a germicidal chamber exit near the bottom of the housing; and
   wherein there is no air flow communication between the first and second air streams.

10. The air purifier of claim 9 wherein the second air stream moves in a substantially vertical direction.

11. The air purifier of claim 10 wherein the first air stream moves in a substantially horizontal direction.

12. The air purifier of claim 9, further comprising a fan positioned in the germicidal chamber.

13. The air purifier of claim 12 wherein the fan is positioned near the bottom of the housing.

14. The air purifier of claim 9 wherein the germicidal chamber is positioned within the electrostatic chamber.

15. The air purifier of claim 9 wherein the germicidal chamber and the electrostatic chamber are positioned side-by-side.

\* \* \* \* \*